(12) United States Patent
Yamaguchi et al.

(10) Patent No.: US 7,186,696 B2
(45) Date of Patent: Mar. 6, 2007

(54) REAGENT AND METHOD FOR MEASURING AMYLASE

(75) Inventors: Masaki Yamaguchi, Toyama (JP); Hiroshi Yoshida, Osaka (JP); Nobutaka Kusaba, Osaka (JP)

(73) Assignees: Toyama University, Toyama (JP); Nipro Corporation, Osaka (JP); Yamaha Hatsudoki Kabushiki Kaisha, Shizuoka (JP)

( * ) Notice: Subject to any disclaimer, the term of this patent is extended or adjusted under 35 U.S.C. 154(b) by 460 days.

(21) Appl. No.: 10/379,094

(22) Filed: Mar. 4, 2003

(65) Prior Publication Data

US 2003/0175842 A1 Sep. 18, 2003

(30) Foreign Application Priority Data

Mar. 7, 2002 (JP) ............................. 2002-062093

(51) Int. Cl.
*A01N 43/04* (2006.01)
(52) U.S. Cl. ....................................................... 514/23
(58) Field of Classification Search ................... 435/4, 435/22

See application file for complete search history.

(56) References Cited

U.S. PATENT DOCUMENTS

| | | | | |
|---|---|---|---|---|
| 4,622,295 A * | 11/1986 | Ikenaka et al. | ................ | 435/22 |
| 4,810,636 A | 3/1989 | Corey | .......................... | 435/14 |
| 5,077,011 A | 12/1991 | Amano et al. | ................. | 422/56 |
| 5,223,219 A | 6/1993 | Subramanian et al. | | |
| 5,334,502 A * | 8/1994 | Sangha | ....................... | 435/7.21 |
| 5,384,245 A | 1/1995 | Kwan | | |
| 2003/0175843 A1 | 9/2003 | Yamaguchi et al. | | |

FOREIGN PATENT DOCUMENTS

| EP | 0 324 912 A2 | 7/1989 |
|---|---|---|
| EP | 0 459 536 A1 | 12/1991 |
| EP | 0 557 021 A2 | 8/1993 |

OTHER PUBLICATIONS

Majima et al, "Determination of alpha-amylase using a new blocked substrate", 1995 Clinica Chimica Acta, vol. 234, pp. 177-179.*
Young et al, "Use of a Competitive Inhibitor in a Kinetic Enzymatic Method for Measuring Ethanol in Serum", 1987 Clinical Chemistry, vol. 33/12, pp. 2296-2298.*
Chatterton et al., "Salivary α-amylase as a Measure of Endogenous Adrenergic Activity," Clinical Physiology, No. 16, 1996, pp. 433-448.
Speirs et al., "The Influence of Sympathetic Activity and Isoprenaline on the Secretion of Amylase from the Human Parotid Gland," Archives of Oral Biology, vol. 19, 1974, pp. 747-752.
Chrousos et al., "The Concepts of Stress and Stress System Disorders," Journal of the American Medical Association, vol. 267, No. 9, Mar. 4, 1992, pp. 1244-1252.
"Flow-injection-type Biosensor System for Salivary Amylase Activity" Biosensors 2002, May 16, 2002.
"Change of Amylase activity on physical stress test" The Japanese Journal of Stress sciences Oct. 29, 2002 (vol. 16(2)).
"Is Saliva an Index for stress Level?" Iyou densi seitaikougaku, vol. 39, No. 3 (2002).
"Stress Monitor Via salivary Amylase Activity" CMC syuppankan Monthly Bio Industry-2002 vol. 10 (10) p. 20-25.
"Analysis of stress reaction by salivary α-amylase" Dai 45 kai nihon daekisen gakkai syourokusyu, vol. 42, 2001.
Toyama daigaku kouhousi Tomuzu magazinn, No. 4 winter 2002.
Toyama News Paper Mar. 2, 2001.
Nihon keizai News Paper Mar. 23, 2001.
Yomiuri News Paper May 2, 2001.
Toyama News Paper Apr. 5, 2002.
Kitanihon News Paper Jul. 10, 2002.
Japanese Journal of Clinical Dentistry of Children Apr. 2002 (vol. 7, No. 4) p. 35-39.
Suganuma T et al., "Study of the action of human salivary alpha-amylase on 2-chloro-4-nitrophenyl alpha-maltotrioside in the present of potassium thiocyanate", *Carbohydrate Reasearch*, Elseview Scientific Publishing Company. Amsterdam, NL vol. 303, No. 2, Sep. 5, 1997.
Winn-Deen E S et al., "Developmental of a direct assay for X-amylase", *Clinical Chemistry*, Amercican Association for Clinical Chemistry. Winston, US vol. 34, No. 10, Oct. 1, 1988.

* cited by examiner

*Primary Examiner*—Christopher R. Tate
*Assistant Examiner*—Amanda P. Wood
(74) *Attorney, Agent, or Firm*—Kilyk & Bowersox, P.L.L.C.

(57) ABSTRACT

An object of the present invention is to provide a means for the measurement of amylase activity that exists in a biological sample such as saliva in a more convenient manner and particularly to provide a means (method and reagent) where a sample containing amylase in high concentration is directly measured without dilution. In the present invention, there has been found a method, which is an enzymatic method using a modified oligosaccharide substrate, comprising adding saccharide such as oligosaccharide that is competitive to the oligosaccharide substrate whereupon amylase activity in an amylase sample having a high activity value can be directly measured without dilution, and a result, the present invention has been achieved.

8 Claims, 5 Drawing Sheets

ND OF INVENTION

REAGENT AND METHOD FOR MEASURING AMYLASE

The present application claims priority from Japanese Patent Application No. 2002/062093, filed Mar. 7, 2002, incorporated by reference herein.

TECHNICAL FIELD

The present invention relates to a reagent for measuring amylase activity and to a method for measuring the same. More particularly, it relates to a reagent and method, which permit to measure amylase activity in a sample having a high amylase activity directly without diluting it. The present invention further relates to a method for testing stress of a subject by the measured value of the saliva amylase activity.

BACKGROUND OF THE INVENTION

Amylase (enzyme number: EC3.2.1.1) is secreted from pancreas, salivary gland and so on, and is mostly distributed in salivary gland and pancreas. Besides those, it is known to be present in muscle, ovary and oviduct as well. It is further known that amylase which is exuded from tissues is present in blood and urine. It is known that amylase value in serum, urine or pancreatic juice shows a high value in a part of functional disorders of pancreas or salivary gland and kidney or liver, or neoplastic disease. With regard to a method for measuring such amylase activity, there have been already known a Caraway method or an enzymatic method using an oligosaccharide substrate, etc. All of those methods are able to measure amylase activity to an extent of thousands IU/L and have been used for the measurement of serum, pancreatic juice, urine sample, etc. in which the normal value of amylase activity is from about tens to hundreds IU/L.

According to the studies in recent years, it has been reported that saliva amylase activity value is correlated to stress of a subject [Japanese journal of medical electronics and biological engineering, 39(3), p. 234–239 (2001), Masaki Yamaguchi, et al.], and a method for measuring amylase activity value in saliva samples has been demanded.

However, normal value of amylase activity in saliva is several ten thousands IU/L, so that it is unable to directly measure amylase activity in saliva by the conventional method. Accordingly, extra operations such as dilution of a sample are necessary and, in addition, dilution to an extent of several hundred times is necessary whereby there is a problem of causing a decrease in the precision of the measurement.

DISCLOSURE OF THE INVENTION

An object of the present invention is to provide a means for measuring amylase activity that exists in a biological sample such as saliva in a more convenient manner, and particularly to provide a means (method and reagent) for measuring a sample that contains amylase in high concentration directly without diluting the same.

The present inventors have found a method, which is an enzymatic method using a modified oligosaccharide substrate, comprising adding saccharide such as oligosaccharide that is competitive to the oligosaccharide substrate whereupon amylase activity in an amylase sample having a high activity value can be directly measured without dilution and, as a result, they have achieved the present invention.

Thus, the present invention comprises the followings.

1. A reagent or reagent kit for measuring amylase activity which is measured by an enzymatic method, comprising at least a modified oligosaccharide which is a substrate and a competitive inhibitor which antagonize said modified oligosaccharide to act competitively.

2. The reagent or reagent kit for measuring amylase activity according to the above 1, wherein the competitive inhibitor is a saccharide which molecular structure is similar to that of the substrate.

3. The reagent or reagent kit for measuring amylase activity according to the above 1, comprising the substrate and the competitive inhibitor in ratios of 2 mmol~500 mmol and 0.01 mol~2 mol, respectively.

4. The reagent or reagent kit for measuring amylase activity according to the above 1, wherein the modified oligosaccharide which is a substrate is an oligosaccharide selected from G2, G3, G4, G5, G6 and G7 and has a reducing end that is modified with a chromogen.

5. The reagent or reagent kit for measuring amylase activity according to the above 4, wherein the chromogen is selected from 4-nitrophenol (PNP), 2-chloro-4-nitrophenol (CNP) and 2,4-dichlorophenol ($Cl_2P$).

6. The reagent or reagent kit for measuring amylase activity according to the above 1, wherein the modified oligosaccharide is selected from the followings;
2-chloro-4-nitrophenol-4-O-β-D-galactopyranosyl-malto side (hereinafter, referred to as GAL-G2-CNP), GAL-G4-CNP, GAL-G5-CNP, 2-chloro-4-nitrophenyl-maltopentaose (hereinafter, referred to as G5-CNP), G6-CNP, G7-CNP, p-nitrophenyl-maltopentaose (hereinafter, referred to as G5-PNP) and G7-PNP.

7. The reagent or reagent kit for measuring amylase activity according to the above 1, wherein the competitive inhibitor is an oligosaccharide or starch.

8. The reagent or reagent kit for measuring amylase activity according to the above 7, wherein the oligosaccharide which is a competitive inhibitor is an oligosaccharide comprising three or more sugars.

9. The reagent or reagent kit for measuring amylase activity according to the above 8, wherein the oligosaccharide which is a competitive inhibitor is selected from maltotriose, maltotetraose and maltopentaose.

10. The reagent or reagent kit for measuring amylase activity according to the above 7, wherein the oligosaccharide which is a competitive inhibitor is maltose.

11. The reagent or reagent kit for measuring amylase activity according to the above 1, wherein the substrate and the competitive inhibitor are liquid.

12. The reagent or reagent kit for measuring amylase activity according to the above 1, wherein the substrate and the competitive inhibitor are in a state of being carried on a support.

13. A method for measuring amylase in a biological sample containing amylase in high concentration, comprising using the reagent or reagent kit for measuring amylase activity according to above 11 or 12.

14. The method for measuring amylase according to the above 13, wherein the biological sample is human saliva, blood or a material derived therefrom.

15. The method for measuring amylase according to the above 14, wherein the biological sample containing amylase is directly measured without dilution.

16. A method for testing stress level of a subject comprising measuring amylase activity in human saliva by the method for measuring amylase according to the above 15.

BEST MODE FOR CARRYING OUT THE INVENTION

Figure 1:
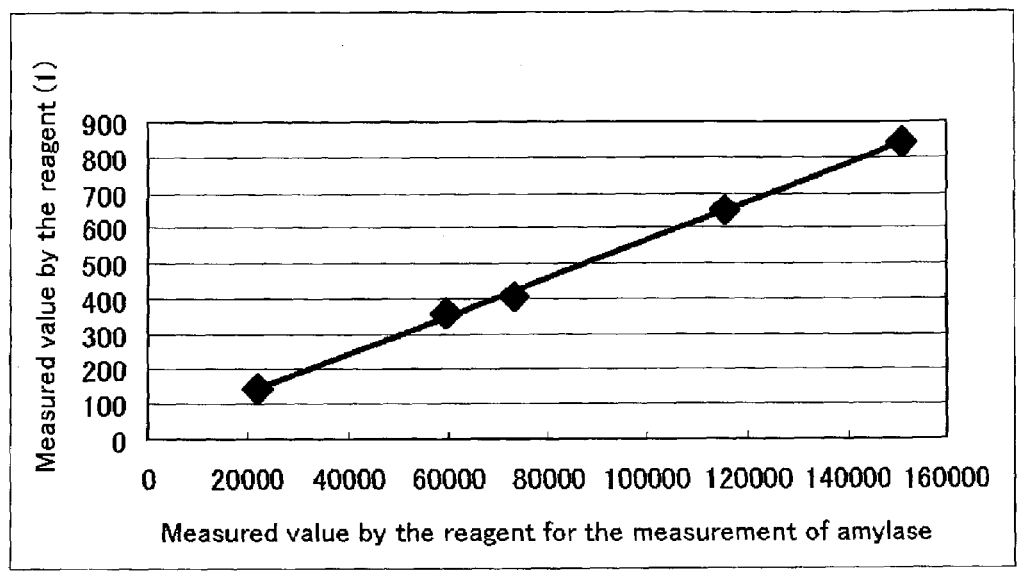
FIG. 1 shows correlation between a result of measurement of a 100-fold diluted sample by Espa Amylase Liquid II and a result of measurement by the reagent (1).

In the present invention, amylase is represented by α-amylase which is mostly secreted from human salivary gland and pancreatic gland. Amylase is a digestive enzyme having a molecular weight of 54,000~62,000 which hydrolyzes polysaccharides such as starch and amylose. It has been known that amylase activity in saliva shows very wide variations depending on one's physical condition and very large personal difference. Although its normal value is around several ten thousands IU/L, it has been known that, even in healthy persons, the value may exceed 100,000 IU/L depending on one's physical condition or habit.

With regard to a substrate used in the present invention for a measurement of amylase activity, a modified oligosaccharide is preferably used. The term "modified" herein means that a compound for labeling which can be discriminated is being linked to the end of, for example, the reducing end of oligosaccharide, and said compound is liberated by amylase or by a coupling enzyme. The numbers of the sugars which comprise said modified oligosaccharide are G2~G7 and, preferably, G2~G5. With regard to the compound for labeling, that which is called chromogen may be generally used and the preferred group is exemplified by 4-nitrophenol (PNP), 2-chloro-4-nitrophenol (CNP) and 2,4-dichlorophenol (Cl$_2$P). Specific examples of the oligosaccharide which is modified with such chromogen are 2-chloro-4-nitrophenol-4-O-β-D-galactopyranosyl-maltoside (hereinafter, referred to as GAL-G2-CNP), GAL-G4-CNP, GAL-G5-CNP, G5-CNP (2-chloro-4-nitrophenyl-maltopentaose), G7-CNP, G5-PNP (p-nitrophenyl-maltopentaose), G6-CNP (2-chloro-p-nitrophenyl-maltotetraose) and G7-PNP. Among those, the particularly preferred ones are GAL-G2-CNP, GAL-G4-CNP and the like where cleavage site upon hydrolysis by amylase is limited to one.

The modified oligosaccharide may be represented by the following formula.

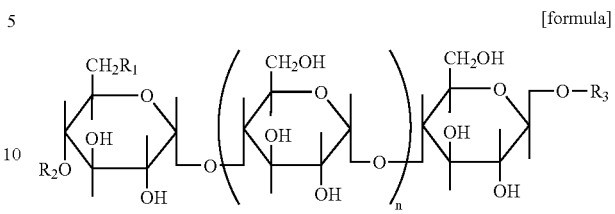

[formula]

In the formula, $R_1$ and $R_2$ each is hydrogen atom or a protecting group. There is no particular limitation for the protecting group. For example, it is an unsubstituted or substituted lower alkyl group, lower alkoxyl or phenyl group, azide group, halogen atom, N-monoalkylcarbamoyloxy group, alkyl or arylsulfonyloxy group or alkyloxy group, α-glucosyl group, α-maltosyl group and β-galactosyl group. $R_1$ and $R_2$ may be cross-linked each other and said cross-linked group may be further substituted. $R_3$ is a signal-generating group such as a group wherein the signal can be optically detected (preferably, coloring aromatic group) and n is 0~5. In the above formula, although —OR$_3$ is in a β-bonded form at position 2 of a glucose having reducing end, it may be in an α-bonded one.

A competitive inhibitor, which competitively acts on the reactivity of the substrate in the present invention, means a compound which antagonizes the modified oligosaccharide which is a substrate, and is competitively affected by amylase. For example, a saccharide which molecular structure is similar to the molecular structure of the substrate is preferably exemplified. To be more specific, starch or an oligosaccharide except for the oligosaccharide used for the modified oligosaccharide may be exemplified. With regard to said oligosaccharide, an oligosaccharide comprising two or more sugars, preferably G2~G7 or, more preferably, G2~G5 is used. To be more specific, it is maltose, maltotriose, maltotetraose or maltopentaose and, most preferably, maltotriose may be exemplified. Incidentally, although G2 compound is not usually suitable as a substrate, it is surprising that said compound could be an extremely preferred competitive inhibitor in the present invention.

The ratio of the substrate and the competitive inhibitor existing in the reagent or the reagent kit for the measurement of amylase activity in the present invention is that the competitive inhibitor is greatly excessive or 1.5- to 100-fold, preferably 2- to 50-fold or, more preferably, 2- to 10-fold to the existing amount of the substrate. To be more specific, the substrate and the competitive inhibitor are contained in the ratios of 2 mmol~500 mmol and 0.01 mol~2 mol, respectively. In the case of a liquid reagent, amount of the substrate is usually adjusted to be in a concentration of about 0.05 mM~1M and, preferably, 2 mM~500 mM.

In the reagent or reagent kit for the measurement of amylase activity in the present invention, the substrate and the competitive inhibitor are in a state of liquid or being carried on a carrier. Said "liquid" means that the substrate and the competitive inhibitor are previously made to be present in an aqueous solution, in an aqueous solution for the optimum stabilizing condition or in a buffer, which is placed in a container for collecting a sample such as a test tube, and a sample such as saliva is added to the container as it is without dilution whereby an amylase reaction is resulted. Said "carried on a support" means a state where the substrate and the competitive inhibitor is fixed with or trapped by a water-insoluble and organic or inorganic carrier. With regard to the shape of said support, thin film is advantageous where the thickness is 100 μm~500 μm or, preferably, 150 μm~400 μm. Since color of the compound for labeling that is liberated is measured by a color discriminating sensor, it is preferred that diffused reflection of light in said thin film is controlled and that the film surface is as uniform as possible. With regard to the material of said thin film, preferred examples are paper, nitrocellulose, Nylon and porous glass, although they are not limited thereto, but many others may be utilized so far as they are able to efficiently carry or hold the substrate and the competitive inhibitor which are defined in the present invention.

In the reaction in the measurment method according to the present invention, a saccharide that is a competitive inhibitor is added to (or made to exist in) the reaction system whereupon amylase in the sample decomposes not only the modified oligosaccharide substrate but also an oligosaccharide that is a competitive inhibitor. In other words, the substrate and the oligosaccharide that is a competitive inhibitor compete in the reaction, and it becomes possible to measure a high amylase activity using the same amount of the substrate.

Although there is no particular limitation for the reaction temperature in the measurement method of the present invention, it is preferably about 25° C.~40° C. With regard to the reaction time, one to ten and several minute(s) will be sufficient and it depends on the type of the substrate and of the coupling enzyme that is used for the reaction upon necessity. There is no particular limitation for the optimum pH and, in the case of liquid reagent, pH may be adjusted, if desired, to 6~8 using an appropriate buffer. If further desired, known activators for α-amylase may be used to accelerate the reaction.

The mechanism for the measurement according to the present invention is that the changes in absorption due to coloration of the sample solution or the sample support are quantitatively grasped on the basis of liberation of chromogen such as CNP or PNP which is a substance used for modification, whereby the amylase activity is determined. Usually, the chromogen can be liberated by the action of a great excessive amylase. If desired, it is also possible to use a enzyme coupling method comprising a reaction where chromogen is liberated by amylase with α-glucosidase, β-glucosidase or the like after hydrolyzing reaction by amylase. In that case, it is necessary to introduce a means for adding an additional enzyme as a reagent.

In the measurement of changes by coloration, a color discriminating sensor is appropriately utilized. It is convenient that the changes in coloration by a reagent carried on a support are measured by means of reflected light or transmitted light. With regard to a light source, light-emitting diode, laser, halogen lamp, or tungsten lamp, etc. is used, although it is not limited thereto. In the measurement of reflected light, there may appropriately used an apparatus for the measurement which satisfies the conditions that angle is 0~45°, distance from the object to be measured is 10 mm~30 mm and sample spot diameter is 1 mm~5 mm.

The method for measuring amylase activity utilizing the reagent or the reagent kit of the present invention thus provided is suitable for a sample containing a high concentration of amylase as a biological sample. For example, saliva, blood, urine, etc. may be used as samples and saliva is most preferred. In the present invention, it is possible to directly measure those samples without diluting them.

The present invention, in which a convenient measurement of amylase activity in human saliva can be performed, makes it possible to provide convenient and effective means for a method for detecting the stress level of a subject. To be more specific, α-amylase activity in saliva collected from a subject in a resting period is measured, and the activity value is recorded, memorized and used as a standard value. After that, α-amylase value of the subject at a certain condition is measured and compared with the standard value that was recorded and memorized in a resting period. When the enzymatic activity is higher than the standard value, it is judged that the subject receives unpleasant stress (distress), while, when it is lower than that, he/she is in comfortable conditions. In addition, the more the difference from the standard value, the higher the stress being received is, and the degree of the stress, which body or mentality receives, can be judged.

Further, when α-amylase activity is continuously measured, it is possible to catch the changes in stress with a lapse of time. When one receives distress, there is a rise in the α-amylase activity in saliva. It is possible to judge a degree of extent of the stress from a size of a positive time gradient at that time. On the contrary, in comfortable conditions with little stress, enzymatic activity of α-amylase lowers, so that it is expressed as a negative time gradient whereby the degree of extent can be judged as well.

It is also possible that α-amylase activity is measured with following time and the changes in enzymatic activity caused by stress that has been loaded during the measuring time are grasped whereby a degree of extent of the stress is judged from size of the changes and time consumed for recovering to the value before loading the stress (standard value).

EXAMPLES

The present invention will now be illustrated in more detail by way of the following examples. The present invention is not limited thereto but anything is within a scope of the technical idea of the present invention so far as it relates to a method for measuring amylase activity on the basis of an enzymatic method containing a competitive inhibitor which competitively acts against a modified oligosaccharide which is a substrate by being antagonistic to the same.

Example 1

The following saccharides were added to the reagent 1 and reagent 2 of Espa Amylase Liquid II (Nipro) which is a reagent for the measurement of amylase activity whereupon reagent solutions ((1)~(3)) containing a substrate and a competitive inhibitor were prepared.

Reagent (1): Each 0.5 mol/L of maltotriose was dissolved.

Reagent (2): Each 0.5 mol/L of maltotetraose was dissolved.

Reagent (3): Each 0.5 mol/L of maltopentaose was dissolved.

Example 2

The following saccharides were added to the reagent 1 and reagent 2 of Espa Amylase Liquid II (Nipro) that is a reagent for the measurement of amylase activity whereupon reagent solutions ((4)~(6)) containing a substrate and a competitive inhibitor were prepared.

Reagent (4): Each 0.1 mol/L of maltotriose was dissolved.

Reagent (5): Each 0.1 mol/L of maltotetraose was dissolved.

Reagent (6): Each 0.1 mol/L of maltopentaose was dissolved.

Example 3

There was prepared a reagent (7) (Test paper) where a substrate and a competitive inhibitor were carried on a carrier by the following preparing method.

Advantec Filter Paper 514A (Toyo Filter Paper) was dipped for 3 minutes in a solution where 70 mmol/L of Gal-G2-CNP, 3.5 mol/L of KSCN and 1 mol/L of maltotetraose were dissolved in a buffer and then dried. The test paper was cut in a size of 7 mm×7 mm.

Example 4

There was prepared a reagent (8) (Test paper) where a substrate and a competitive inhibitor were carried on a carrier by the following preparing method.

Advantec Filter Paper 514A (Toyo Filter Paper) was dipped for 3 minutes in a solution where 140 mmol/L of Gal-G2-CNP, 7 mol/L of KSCN and 0.5 mol/L of maltopentaose were dissolved in a buffer and then dried. The test paper was cut in a size of 7 mm×7 mm.

Test Example 1

Amylase activity was measured using the reagent of Example 1 according to the following treatments.

1. Saliva samples were collected from 5 healthy volunteers (samples a~e).

2. Amylase activity values of the above samples and a negative control (physiological saline) were measured by Espa Amylase Liquid II (Nipro) which is a reagent for measurement of amylase activity (control). Espa Amylase Liquid II is a reagent for measurement of amylase activity on the basis of an enzymatic method using Gal-G2-CNP and is able to measure amylase to an extent of 2,000 IU/L. Autoanalyzer 7170 (Hitachi) was used for the measurement. Since amylase activity value in saliva is higher than the measuring limit, the measurement was not possible as it was. Therefore, each of the samples diluted to an extent of 100-fold using 1% (W/V) BSA (meaning a 1% (W/V) solution of bovine serum albumin in physiological saline; hereinafter, this has the same meaning as well) was measured instead. Result of the measurement is shown in Table 1. Amylase activities of the samples a~e were 21800, 59700, 73200, 116000 and 151000 IU/L, respectively.

TABLE 1

|  | Measured Value |
| --- | --- |
| Sample a | 218 |
| Sample b | 597 |
| Sample c | 732 |
| Sample d | 1155 |
| Sample e | 1513 |

3. The samples a~e without dilution were subjected to the measurement of amylase activity values using the reagents (1)~(3) of Example 1. Autoanalyzer 7170 (Hitachi) was used for the measurement and the measuring conditions such as parameters for the analyzer were as same as those in 2. Result of the measurement is as shown in Table 2.

TABLE 2

|  | Measured Value by Reagent (1) | Measured Value by Reagent (2) | Measured Value by Reagent (3) |
| --- | --- | --- | --- |
| Sample a | 143 | 49 | 44 |
| Sample b | 360 | 190 | 141 |
| Sample c | 406 | 211 | 150 |
| Sample d | 649 | 325 | 242 |
| Sample e | 842 | 436 | 312 |

Figure 2:
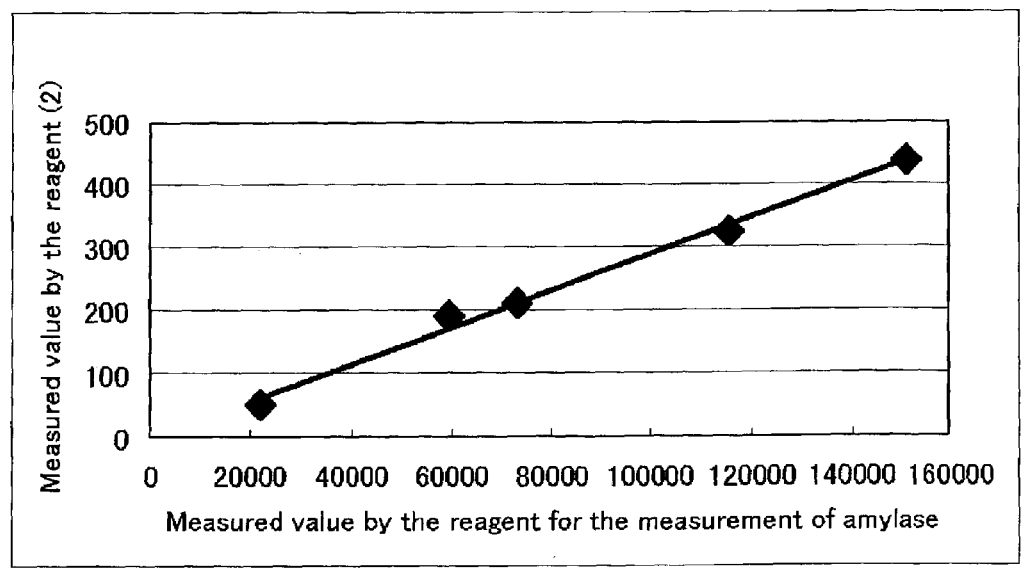
FIG. 2 shows correlation between a result of measurement of a 100-fold diluted sample by Espa Amylase Liquid II and a result of measurement by the reagent (2).
Figure 3:
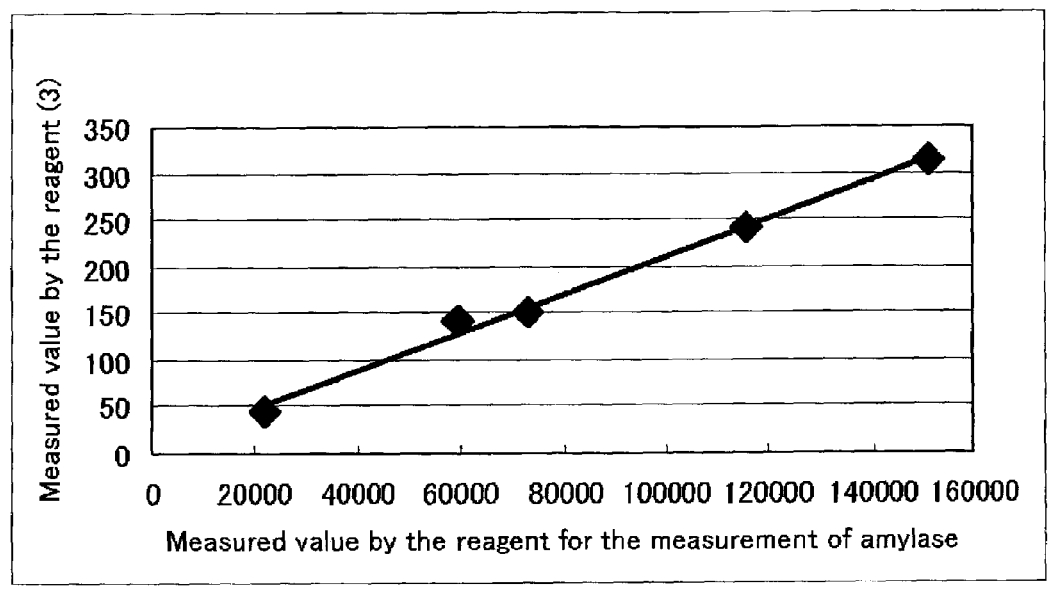
FIG. 3 shows correlation between a result of measurement of a 100-fold diluted sample by Espa Amylase Liquid II and a result of measurement by the reagent (3).

Correlation between the result of the measurement of 100-fold diluted samples by Espa Amylase Liquid II and the result of the measurement by the reagents (1)~(3) are as shown in FIG. 1 to FIG. 3. All of the results showed high correlation with correlation coefficients of r=1.00, 1.00 and 1.00, respectively. When the measured values obtained by using the reagent (1)~(3) were made 171-fold, 361-fold and 473-fold, respectively, the resulting values were nearly the same as those in the conventional methods. Thus, it was shown that the reagent of the present invention was able to directly measure the amylase activity value of saliva sample without diluting the sample.

Test Example 2

Amylase activity was measured using the reagent of Example 2 according to the following treatments.

1. Saliva samples were collected from 3 healthy volunteers (samples f~h).

2. Amylase activity values of the above samples and a negative control sample (physiological saline) were measured by Espa Amylase Liquid II (Nipro) which is a reagent for measurement of amylase activity. Autoanalyzer 7170 (Hitachi) was used for the measurement. Since amylase activity value in saliva is higher than the measuring limit, the measurement was not possible as it was. Therefore, each of the samples diluted to an extent of 100-fold using 1% (W/V) BSA was measured instead. Result of the measurement is shown in Table 3.

TABLE 3

|  | Measured Value |
| --- | --- |
| Sample f | 370 |
| Sample g | 295 |
| Sample h | 190 |
| Physiological Saline | 0 |

3. Each of the samples without dilution was subjected to the measurement of amylase activity values using the reagents (4)~(6) of Example 2. Autoanalyzer 7170 (Hitachi) was used for the measurement and the measuring conditions were as same as those in 2. Result of the measurement is as shown in Table 4. HI means that the measurement was not possible because of being out of the measuring limit.

TABLE 4

|  | Measured Value by Reagent (4) | Measured Value by Reagent (5) | Measured Value by Reagent (6) |
| --- | --- | --- | --- |
| Sample f | HI | 1992 | 845 |

TABLE 4-continued

|  | Measured Value by Reagent (4) | Measured Value by Reagent (5) | Measured Value by Reagent (6) |
|---|---|---|---|
| Sample g | 1948 | 1493 | 535 |
| Sample h | 1438 | 883 | 376 |
| Physiological Saline | 0 | 0 | 0 |

Figure 4:
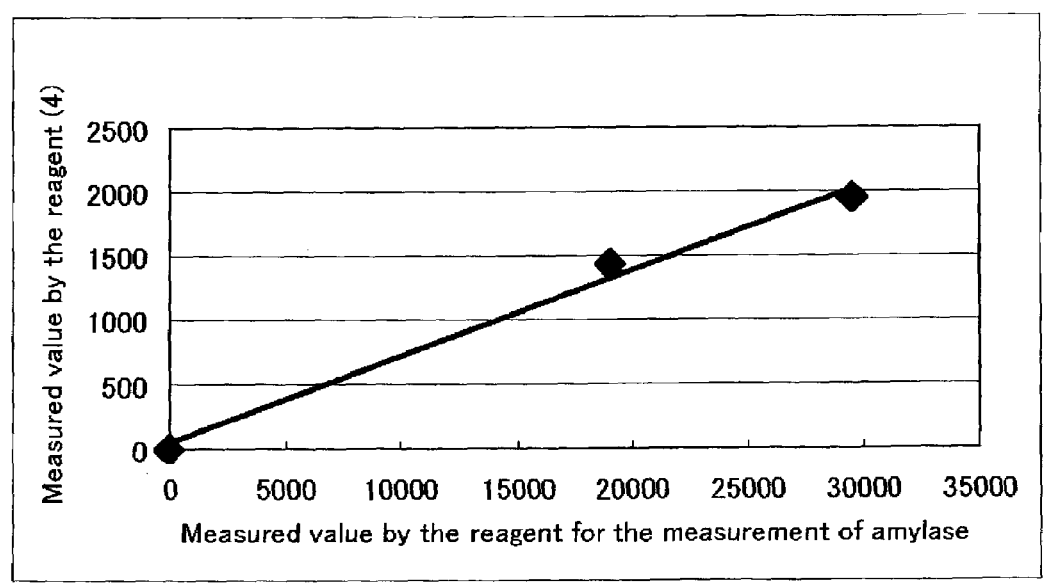
FIG. 4 shows correlation between a result of measurement of a 100-fold diluted sample by Espa Amylase Liquid II and a result of measurement by the reagent (4).
Figure 5:
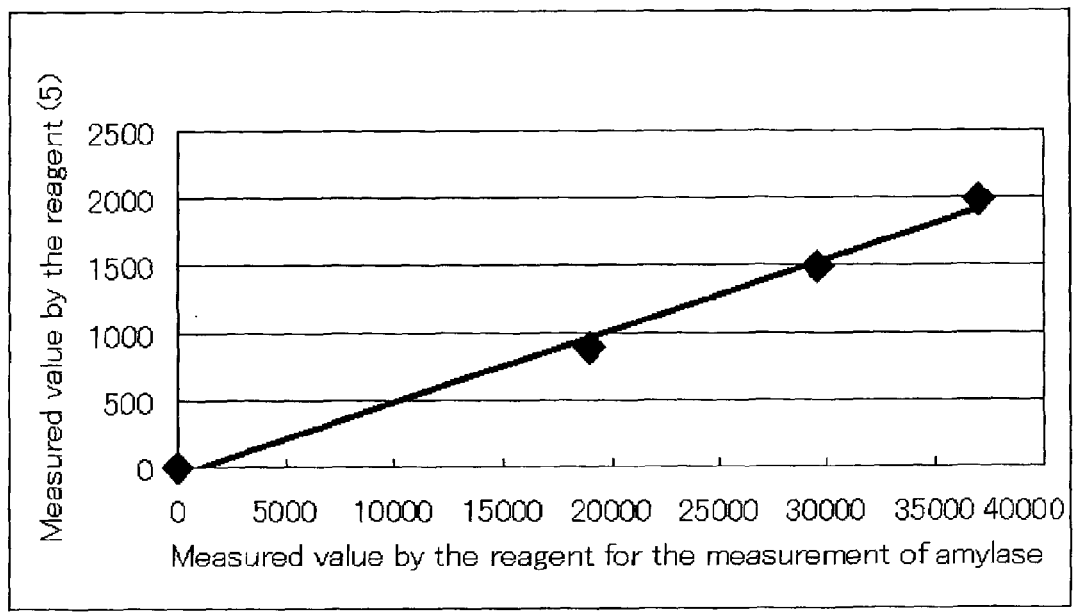
FIG. 5 shows correlation between a result of measurement of a 100-fold diluted sample by Espa Amylase Liquid II and a result of measurement by the reagent (5).
Figure 6:
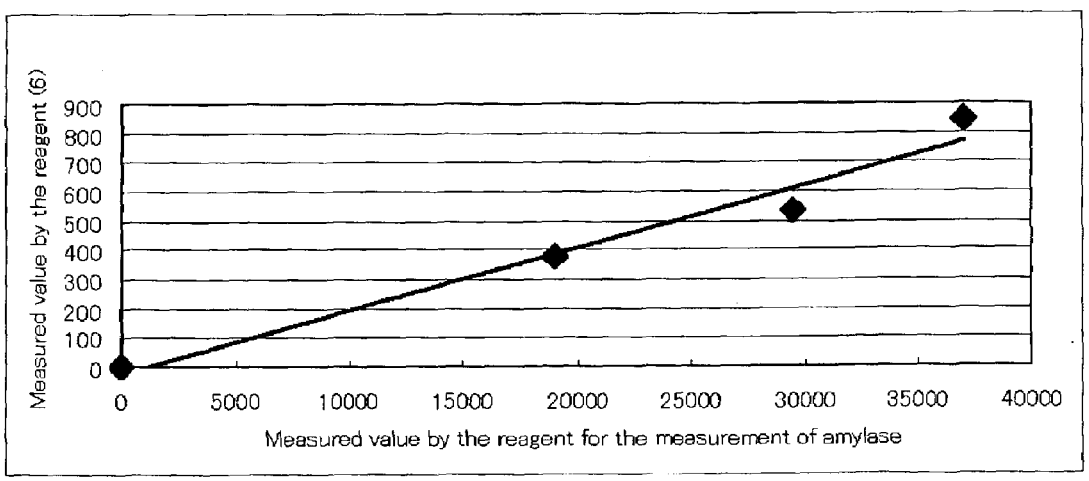
FIG. 6 shows correlation between a result of measurement of a 100-fold diluted sample by Espa Amylase Liquid II and a result of measurement by the reagent (6).

Correlation between the result of the measurement of 100-fold diluted samples by Espa Amylase Liquid II and the result of the measurement by the reagents (4)~(6) is as shown in FIG. 4 to FIG. 6. A high linearity with r=0.99, 0.99 and 0.89 was resulted. When the measured values obtained by using the reagent (4)~(6) were made 14-fold, 20-fold and 50-fold, respectively, the resulting values were nearly the same as those in the conventional methods. Thus, it was shown that the reagent of the present invention was able to directly measure the amylase activity value of saliva sample without diluting the sample.

Test Example 3

Amylase activity was measured using the reagent of Example 1 according to the following treatments.

1. Saliva sample d used in Test Example 1 was diluted with 1% (W/V) BSA to an extent of 0.2-, 0.4-, 0.6- and 0.8-fold concentrations.
2. Amylase activity values of the above samples and a negative control sample (physiological saline) were measured by Espa Amylase Liquid II (Nipro) which is a reagent for measurement of amylase activity. Autoanalyzer 7170 (Hitachi) was used for the measurement. Since amylase activity value in saliva is higher than the measuring limit, the measurement was not possible as it was. Therefore, each of the samples diluted to an extent of 100-fold using 1% (W/V) BSA was measured instead. Result of the measurement is shown in Table 5.

TABLE 5

|  | Measured Value |
|---|---|
| Sample d | 1155 |
| Sample d × 0.8-fold | 920 |
| Sample d × 0.6-fold | 689 |
| Sample d × 0.4-fold | 515 |
| Sample d × 0.2-fold | 240 |
| Physiological Saline | 0 |

3. Similarly, each of the samples without dilution was subjected to the measurement of amylase activity values using the reagents (3) prepared in Example 1. Autoanalyzer 7170 (Hitachi) was used for the measurement and the measuring conditions were as same as those in 2. Result of the measurement is as shown in Table 6.

TABLE 6

|  | Measured Value |
|---|---|
| Sample d | 242 |
| Sample d × 0.8-fold | 176 |
| Sample d × 0.6-fold | 135 |
| Sample d × 0.4-fold | 88 |

TABLE 6-continued

|  | Measured Value |
|---|---|
| Sample d × 0.2-fold | 43 |
| Physiological Saline | 0 |

Figure 7:
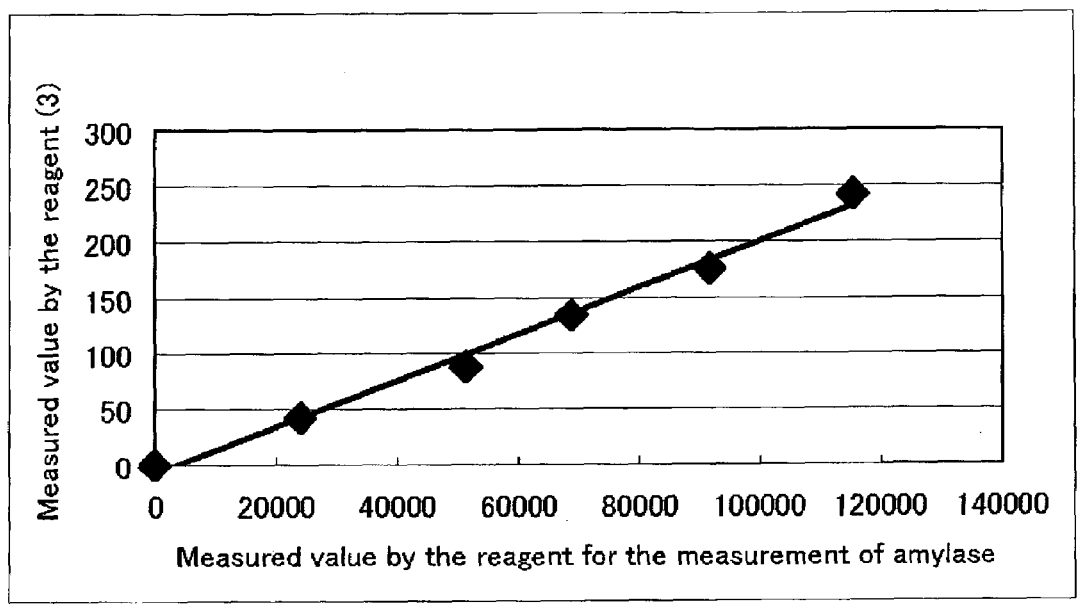
FIG. 7 shows correlation between a result of measurement of a 100-fold diluted sample by Espa Amylase Liquid II and a result of measurement by the reagent (3).

Correlation between the result of the measurement of 100-fold diluted samples by Espa Amylase Liquid II and the result of the measurement by the reagent (3) is as shown in FIG. 7 where a high linearity with r=0.99 was resulted. When the measured values obtained by using the reagent (3) were made 473-fold, the resulting values were nearly the same as those in the conventional methods whereby it was shown that the reagent of the present invention was able to directly measure the amylase activity value of saliva sample without diluting the sample.

Test Example 4

Amylase activity was measured using the reagent prepared in Example 3 according to the following treatments.

1. Saliva sample was collected from a healthy volunteer (sample i) and the sample was diluted with 1% (W/V) BSA to an extent of 0.2-, 0.4-, 0.6- and 0.8-fold concentrations.
2. Amylase activity values of the above samples were measured by Espa Amylase Liquid II (Nipro) which is a reagent for measurement of amylase activity. Autoanalyzer 7170 (Hitachi) was used for the measurement. Since amylase activity value in saliva is higher than the measuring limit, the measurement was not possible as it was. Therefore, each of the samples diluted to an extent of 100-fold using 1% (W/V) BSA was measured instead. Result of the measurement is shown in Table 7.

TABLE 7

|  | Measured Value |
|---|---|
| Sample i | 1107 |
| Sample i × 0.8-fold | 886 |
| Sample i × 0.6-fold | 679 |
| Sample i × 0.4-fold | 438 |
| Sample i × 0.2-fold | 229 |

3. Amylase activity value of the sample shown in 1. was measured using the reagent (7). In the measurement, there was used C mode of a color-discriminating sensor CZ-VI of Keyence. The sample (3 μL) was dropped into the reagent (7) which was prepared in Example 3, followed by determining the difference of the measured values obtained by the sensor between before and one-minute after the reaction. Result of the measurement is as shown in Table 8.

TABLE 8

|  | Measured Value |
|---|---|
| Sample i | 65 |
| Sample i × 0.8-fold | 43 |
| Sample i × 0.6-fold | 31 |
| Sample i × 0.4-fold | 22 |
| Sample i × 0.2-fold | 9 |

Figure 8:
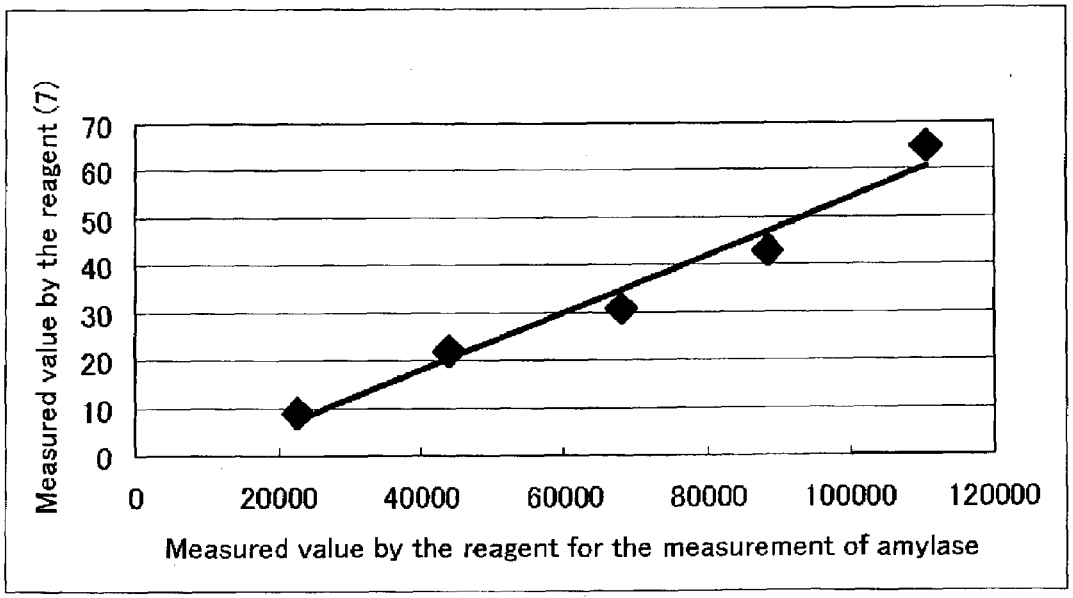
FIG. 8 shows correlation between a result of measurement of a 100-fold diluted sample by Espa Amylase Liquid II and a result of measurement by the reagent (7).

Correlation between the result of the measurement of 100-fold diluted samples by Espa Amylase Liquid II and the result of the measurement by the reagent (7) is as shown in FIG. 8. A high correlation with r=0.98 was resulted.

When the measured values obtained by using the reagent (7) were made 2100-fold, the resulting values were nearly the same as those in the conventional methods whereupon it was shown that the reagent of the present invention was able to directly measure the amylase activity value of saliva sample without diluting the sample.

Test Example 5

Amylase activity was measured for the sample f that were used in Test Example 2 and the diluted samples thereof, using the reagent (8) prepared in Example 4. In the measurement, there was used C mode of a color-discriminating sensor CZ-VI of Keyence. The sample (3 μL) was dropped into the reagent (8), followed by determining the difference of the measured values obtained by the sensor between before and one-minute after the reaction. Result of the measurement is as shown in Table 9.

TABLE 9

| | Measured Values |
|---|---|
| Sample i | 223 |
| Sample i × 0.8-fold | 150 |
| Sample i × 0.6-fold | 135 |
| Sample i × 0.4-fold | 87 |
| Sample i × 0.2-fold | 23 |

Figure 9:
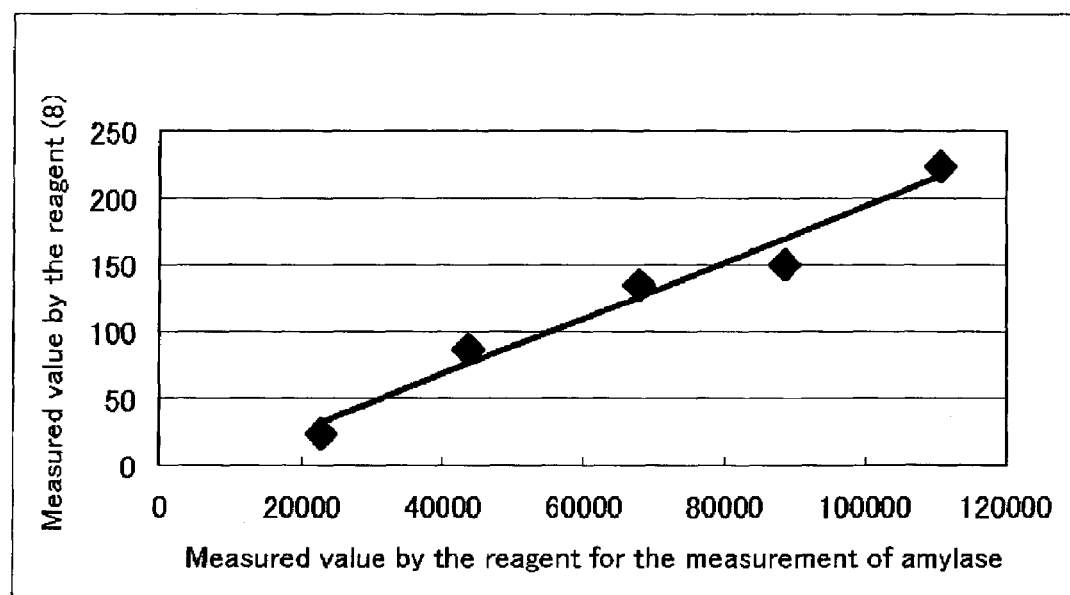
FIG. 9 shows correlation between a result of measurement of a 100-fold diluted sample by Espa Amylase Liquid II and a result of measurement by the reagent (8).

Correlation between the result of the measurement of 100-fold diluted samples by Espa Amylase Liquid II and the result of the measurement by the reagent (8) is as shown in FIG. 9 where there was resulted a high correlation with r=0.98. When the measured values obtained using by the reagent (8) were made 500-fold, the resulting values were nearly the same as those in the conventional methods whereupon it was shown that the reagent of the present invention was able to directly measure the amylase activity value of saliva sample without diluting the sample.

INDUSTRIAL APPLICABILITY

As mentioned hereinabove, there is provided in accordance with the present invention a reagent for the measurement of amylase activity on the basis of an enzymatic method containing a modified oligosaccharide which is a substrate and a competitive inhibitor which acts in a competitive manner to the reactivity of the substrate and, when amylase activity is measured using the reagent, it is now possible to measure the amylase activity in a quite convenient, quick and effective manner, whereby a technique can be established in which stress of a subject can be judged on the spot within a short period.

The invention claimed is:

1. A reagent for measuring amylase activity which is measured by an enzymatic method, said reagent comprising at least a modified oligosaccharide which is a substrate, and a competitive inhibitor which antagonizes said modified oligosaccharide, wherein the substrate and the competitive inhibitor are carried on a water-insoluble support, and further wherein said modified oligosaccharide is an oligosaccharide selected from G2, G3, G4, G5, G6, and G7 and has a reducing end that is modified with a chromogen; and said competitive inhibitor is an oligosaccharide or starch.

2. The reagent for measuring amylase activity according to claim 1, wherein the competitive inhibitor is a saccharide with a molecular structure similar to that of the substrate.

3. The reagent for measuring amylase activity according to claim 1, comprising the substrate and the competitive inhibitor in ratios of 2 mmol.about.500 mmol and 0.01 mol.about.2 mol, respectively.

4. The reagent for measuring amylase activity according to claim 1, wherein the chromogen is selected from 4-nitrophenol (PNP), 2-chloro-4-nitrophenol (CNP) and 2,4-dichlorophenol (Cl2P).

5. The reagent for measuring amylase activity according to claim 1, wherein the modified oligosaccharide is selected from the followings; 2-chloro-4-nitrophenol-4-O-.beta.-D-galactopyranosyl-malto side (hereinafter, referred to as GAL-G2-CNP), GAL-G4-CNP, GAL-G5-CNP, G5-CNP, G6-CNP, G7-CNP, G5-PNP and G7-PNP.

6. The reagent for measuring amylase activity according to claim 1, wherein the competitive inhibitor is an oligosaccharide comprising three or more sugars.

7. The reagent for measuring amylase activity according to claim 1, wherein the competitive inhibitor is an oligosaccharide selected from maltotriose, maltotetraose and maltopentaose.

8. The reagent for measuring amylase activity according to claim 1, wherein the competitive inhibitor is an oligosaccharide and is maltose.

* * * * *